United States Patent [19]

Houlihan et al.

[11] B  3,985,729

[45]  Oct. 12, 1976

[54] SUBSTITUTED 7,12-METHANO DIBENZAZOCINES

[75] Inventors: William H. Houlihan, Mountain Lakes; Jeffrey Nadelson, Lake Parsippany, both of N.J.

[73] Assignee: Sandoz, Inc., E. Hanover, N.J.

[22] Filed: Dec. 23, 1974

[21] Appl. No.: 536,935

[44] Published under the second Trial Voluntary Protest Program on January 13, 1976 as document No. B 536,935.

[52] U.S. Cl. .................... 260/239 D; 260/239 BB; 424/258
[51] Int. Cl.² ....................................... C07D 225/04
[58] Field of Search .................. 260/239 D, 239 BB

[56] References Cited

UNITED STATES PATENTS

| | | |
|---|---|---|
| 3,496,165 | 2/1970 | Houlihan et al. ............... 260/239 D |
| 3,642,777 | 2/1972 | Houlihan et al. ............... 260/239 D |

*Primary Examiner*—Richard J. Gallagher
*Assistant Examiner*—D. B. Springer
*Attorney, Agent, or Firm*—Gerald D. Sharkin; Robert S. Honor; Thomas O. McGovern

[57] ABSTRACT

Substituted 7,12-methano-dibenzazocines, e.g., 7,13-dihydro-6,12-dimethyl-7,12-methano-6H-dibenz[c,f]azocine, are prepared by cyclizing 3-benzylamino-alkyl-indan-1-ols and are useful as anti-inflammatory agents.

15 Claims, No Drawings

SUBSTITUTED 7,12-METHANO DIBENZAZOCINES

This invention relates to 7,12-methano-dibenzazocine derivatives. In particular, it relates to 12-lower alkyl substituted 7,12-methano-dibenzazocines, intermediates for their preparation and their use in pharmaceutical compositions.

The compounds of this invention may be represented by the following structural formula:

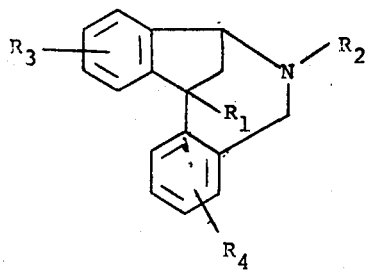

(I)

where
- $R_1$ is straight chain lower alkyl, i.e., alkyl having 1 to 4 carbon atoms, e.g., methyl, ethyl, butyl, and the like;
- $R_2$ is hydrogen or lower alkyl i.e., alkyl having 1 to 4 carbon atoms, e.g., methyl, ethyl, isopropyl, and the like;
- $R_3$ and $R_4$ each independently is hydrogen, halo having an atomic weight of about 19 to 35, lower alkyl as defined above, or lower alkoxy, i.e., alkoxy having 1 to 4 carbon atoms, e.g., methoxy, ethoxy, isopropoxy, butoxy, and the like, or a pharmaceutically acceptable acid addition salt thereof.

The compounds of formula (I) may be prepared in accordance with the following reaction scheme:

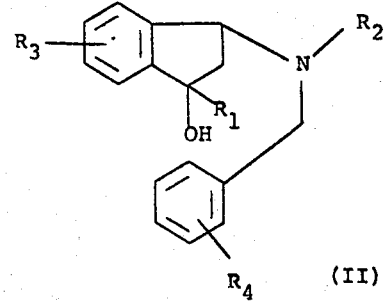

(II)

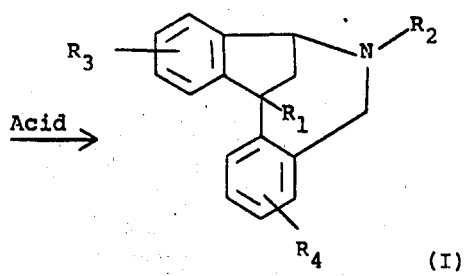

(I)

where $n$, $R_1$, $R_2$, $R_3$ and $R_4$ are as defined above.

The compounds of formula (I) are prepared by cyclizing a compound of the formula (II) in a strong acid media. The strongly acid media can be provided by any strong acid but polyphosphoric acid or concentrated sulfuric acid are preferred. Although a solvent is not required, it is preferred that the reaction be carried out in excess acid. The temperature at which the reaction is run is not critical, but it is preferred that the reaction be carried out between about 80°C to 120°C., preferably 100°C with polyphosphoric acid and between about −10°C to +10°C, especially 0°C, with concentrated sulfuric acid. The time of the reaction also is not critical, but it is preferred that the reaction be run for 2 to 8 hours, in particular, about 5 hours. The compounds of formula (I) are isolated by conventional techniques, e.g., extraction and recrystallization.

The compound of formula (II) may be prepared in accordance with the following reaction scheme:

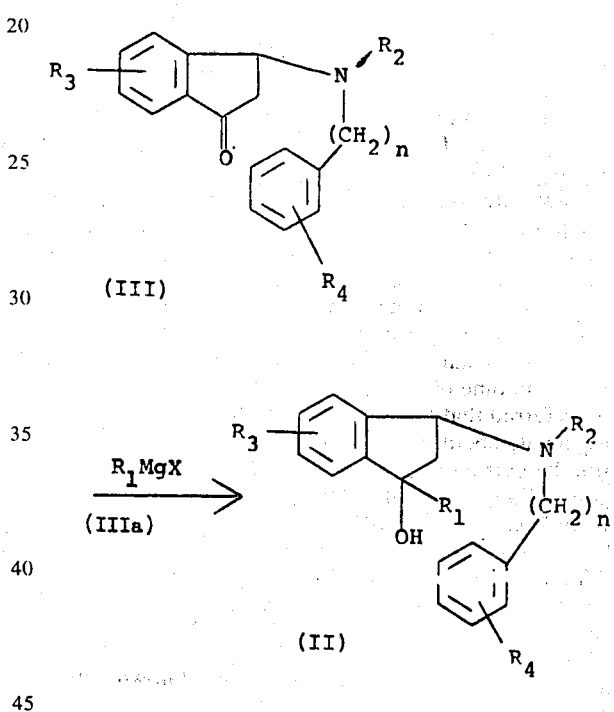

where $n$, $R_1$, $R_2$, $R_3$, and $R_4$ are as defined above.

The compounds of formula (II) are prepared by reactng a Grignard reagent of the formula (IIIa) with a compound of the formula (III) in an inert solvent. It is preferred that the reaction be carried out in an inert solvent such as ethers, e.g., diethyl ether, tetrahydrofuran, and the like or aromatic hydrocarbons, e.g., benzene, toluene, xylene, and the like, especially tetrahydrofuran. The temperature at which the reaction is carried out is not critical, but it is preferred that the reaction be carried out between about 0°C to 200°C., preferably between about 30°C to 150°C., especially at the reflux temperature of the reaction medium. The time of the reaction also is not critical, but it is preferred that the reaction be run for 1 hour to 24 hours, especially 2 hours to 16 hours. It is also preferred that the reaction be carried out in an inert atmosphere such as argon, helium or nitrogen, preferably nitrogen. The compounds of formula (II) are isolated by conventional techniques, e.g., evaporation and recrystallization.

The compounds of formula (III) may be prepared as follows:

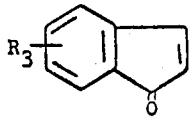

(IV)

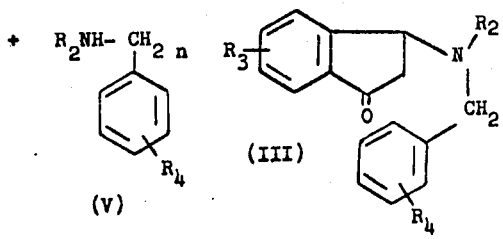

where $n$, $R_2$, $R_3$ and $R_4$ are as defined above.

The compounds of formula (III) are prepared by reacting a compound of the formula (IV) with a compound of the formula (V). Although a solvent is not required, it is preferred that the reaction be carried out in an inert solvent, e.g., a hydrocarbon, such as hexane, heptane, benzene, toluene and the like, or a halogenated hydrocarbon such as chloroform, carbon tetrachloride and the like. The temperature at which the reaction is carried out is not critical, but it is preferred that the reaction be carried out between about 60°C to 180°C, especially at the reflux temperature of the reaction. The time of the reaction also is not critical, but it is preferred that the reaction be run for 10 to 30 hours, especially about 20 hours. It is preferred that the reaction be carried out in an inert atmosphere such as argon, helium, or nitrogen, preferably nitrogen. The compounds of formula (III) are isolated by conventional techniques, e.g., extraction and filtration.

Many of the compounds of formula (IIIa), (IV) and (V) are known and may be prepared by methods disclosed in the literature. The compounds of formula (IIIa), (IV) and (V) not specifically described may be prepared by analogous methods using known starting materials.

The compounds of formula (I) are useful because they possess pharmacological activity in animals. In particular, the compounds of formula (I) are useful as anti-inflammatory agents, as indicated by their activity in rats dosed orally with 25 to 105 milligrams per kilogram of animal body weight of test compound using the acute carrageenan-induced edema procedure substantially as described by Winter (Proc. Soc. Exptl. Biol., 111:544, 1962).

When the compounds are employed for the above utility, they may be combined with one or more pharmaceutically acceptable carriers or adjuvants, and may be administered orally in such forms as tablets, capsules, elixirs, suspensions and the like, or parenterally in the form of an injectable solution or suspension. Depending upon the compound employed and the mode of administration, the exact dosage utilized may vary.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid and accordingly, are included within the scope of the invention. Representative of the acid addition salts are the mineral acid salts, such as the hydrochloride, hydrobromide, sulfate, phosphate and the like and the organic acid salts, such as the succinate, benzoate, acetate, p-toluenesulfonate, benzenesulfonate and the like.

The anti-inflammatory effective dosage of the compounds of formula (I) will depend on the particular compound employed, the method of administration and the severity of the condition being treated. In general, satisfactory results are obtained when these compounds are administered in the treatment of inflammations at a daily dosage of about 2 milligrams to about 200 milligrams per kilogram of animal body weight, preferably orally. This daily dosage is preferably administered 2 to 4 times a day, or in sustained release form. For most large mammals, such as primates, the total daily dosage is from about 150 milligrams to about 1500 milligrams. Dosage forms suitable for internal use comprise from about 37.5 milligrams to about 750 milligrams of the active compound in intimate admixture with a solid or liquid pharmaceutically acceptable carrier or diluent.

A representative formulation suitable for oral administration 2 to 4 times a day in the treatment of inflammation is a capsule prepared by standard encapsulating techniques which contains the following:

| Ingredients | Weight (mg) |
| --- | --- |
| 7,13-dihydro-6,12-dimethyl-7,12-methano-6H-dibenz[c,f]azocine | 100 |
| Inert solid diluent (starch, lactose, kaolin) | 200 |

EXAMPLE 1

7,13-dihydro-6,12-dimethyl-7,12-methano-6H-dibenz[c,f]azocine

Step A: 3-benzylmethylamino-1-indanone

A mixture of 10.0 grams (0.069 mole) of 1-indanone and 18.2 grams of N-methylbenzylamine (0.154 mole) in 250 ml of carbon tetrachloride is refluxed under nitrogen for 20 hours. The mixture is cooled and extracted with 2N hydrochloric acid after which the aqueous acid is cooled and made basic by the addition of 50% sodium hydroxide solution. The basic mixture is extracted with ether, dried over magnesium sulfate and evaporated in vacuo. The solid residue is triturated with pentane to give 3-benzylmethylamino-1-indanone.

When the above procedure is carried out using an equivalent amount of:
 a. benzylamine;
 b. N-ethyl-benzylamine;
 c. N-methyl-p-chlorobenzylamine;
 d. N-methyl-p-methylbenzylamine or
 e. N-methyl-p-methoxybenzylamine
in place of the N-methylbenzylamine used therein, there is obtained
 a. 3-benzylamino-1-indanone;
 b. 3-benzylethylamino-1-indanone;
 c. 3-(p-chlorobenzylmethylamino)-1-indanone;
 d. 3-(p-methylbenzylmethylamino)-1-indanone or
 e. 3-(p-methoxybenzylmethylamino)-1-indanone, respectively.

Following the procedure of this example but using in place of the 2-methyl-1-indanone an equivalent amount of:
a. 5-chloro-1-indenone;
b. 5-methyl-1-indenone or
c. 5-methoxy-1-indenone,
there is obtained;
a. 3-benzylmethylamino-5-chloroindan-1-one;
b. 3-benzylmethylamino-5-methylindan-1-one; or
c. 3-benzylmethylamino-5-methoxyindan-1-one, respectively Step B: 3-benzylmethylamino-1-methylindan-1-ol In 35 milliliters of tetrahydrofuran, 4 grams methyl bromide is dissolved. One quarter of this solution is then added to 1 gram of magnesium, previously washed with chloroform, and refluxed with tetrahydrofuran for 20 minutes; and this mixture is refluxed 4 hours to initiate reaction. Additional methyl bromide solution is thereafter added to maintain the refluxing without further heating. After the addition has been completed 10 grams of 3-benzylmethylaminoindan-1-one is added and the mixture is refluxed for 2 hours. The reactants are allowed to stand overnight and then poured onto ice-cold ammonium chloride solution. Tetrahydrofuran is added and the two layers formed are allowed to separate. The solvent layer is decanted off and the aqueous layer is extracted twice with 10 milliliters of tetrahydrofuran which are decanted off and combined with the remaining solvent layer. The organic phase is dried over anhydrous magnesium sulphate, filtered and evaporated to dryness to yield 3-benzylmethylamino-1-methylindan-1-ol as a yellow oil.

When the above procedure is carried out using an equivalent amount of:
a. 3-benzylamino-1-indanone;
b. 3-benzylethylamino-1-indanone;
c. 3-(p-chlorobenzylmethylamino)-1-indanone;
d. 3-(p-methylbenzylmethylamino)-1-indanone;
e. 3-(p-methoxybenzylmethylamino)-1-indanone;
f. 3-benzylmethylamino-5-chloroindan-1-one;
g. 3-benzylmethylamino-5-methylindan-1-one or
h. 3-benzylmethylamino-5-methoxyindan-1-one
in place of the 3-benzylmethylamino-1-methylindan-1-one, there is obtained
a. 3-benzylamino-1-methylindan-1-ol;
b. 3-benzylethylamino-1-methylindan-1-ol;
c. 3-(p-chlorobenzylmethylamino)-1-methylindan-1-ol;
d. 3-(p-methylbenzylmethylamino)-1-methylindan-1-ol;
e. 3-(p-methoxybenzylmethylamino)-1-methylindan-1-ol;
f. 3-benzylmethylamino-1-methyl-5-chloroindan-1-ol;
g. 3-benzylmethylamino-1-methyl-5-methylindan-1-ol or
h. 3-benzylmethylamino-1-methyl-5-methoxyindan-1-ol, respectively.

Step C: 7,13-dihydro-6,12-dimethyl-7,12-methano-6H-dibenzo[c,f]azocine

To 100 grams of polyphosphoric acid at 100°C is added 10 grams (0.0375 mole) of 3-benzylmethylamino-1-methyl-indan-1-ol. The mixture is heated at 100° for 5 hours, and then poured onto ice. The mixture is made basic by the addition of solid sodium hydroxide, and the basic solution is extracted with ether. The ether phase is dried over magnesium sulfate, filtered and treated with gaseous hydrochloric acid. The resulting precipitate is filtered to give 7,13-dihydro-6,12-dimethyl-7,12-methano-6H-dibenz[c,f]azocine hydrochloride (m.p. 180°-181°) after drying.

The 7,13-dihydro-6,12-dimethyl-7,12-methano-6H-dibenz[c,f]azocine of this example is an effective anti-inflammatory agent when administered orally to a mammal in need of such treatment at a dose of 100 milligrams 2 to 4 times a day.

Following the above procedure but using an equivalent amount of
a. 3-benzylamino-1-methylindan-1-ol;
b. 3-benzylethylamino-1-methylindan-1-ol;
c. 3-(p-chlorobenzylmethylamino)-1-methylindan-1-ol;
d. 3-(p-methylbenzylmethylamino)-1-methylindan-1-ol;
e. 3-(p-methoxybenzylmethylamino)-1-methylindan-1-ol;
f. 3-benzylmethylamino-1-methyl-5-chloroindan-1-ol;
g. 3-benzylmethylamino-1-methyl-5-methylindan-1-ol or
h. 3-benzylmethylamino-1-methyl-5-methoxyindan-1-ol,
in place of the 3-benzylmethylamino-1-methylindan-1-ol, there is obtained the hydrochloride salt of
a. 7,13-dihydro-12-methyl-7,12-methano-6H-dibenz[c,f]azocine
b. 7,13-dihydro-6-ethyl-12-methyl-7,12-methano-6H-dibenz[c,f]azocine
c. 2-chloro-7,13-dihydro-6,12-dimethyl-7,12-methano-6H-dibenz[c,f]azocine;
d. 7,13-dihydro-2,6,12-trimethyl-7,12-methano-6H-dibenz[c,f]azocine;
e. 7,13-dihydro-6,12-dimethyl-2-methoxy-7,12-methano-6H-dibenz[c,f]azocine;
f. 9-chloro-7,13-dihydro-6,12-dimethyl-7,12-methano-6H-dibenz[c,f]azocine;
g. 7,13-dihydro-6,9,12-trimethyl-7,12-methano-6H-dibenz[c,f]azocine or
h. 7,13-dihydro-6,12-dimethyl-9-methoxy-7,12-methano-6H-dibenz[c,f]azocine, respectively.

What is claimed is:

1. A compound of the formula:

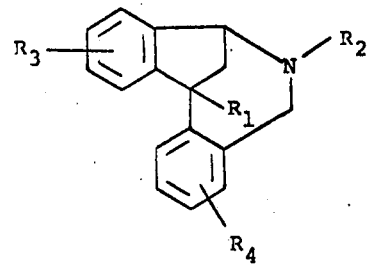

where
$R_1$ is straight chain lower alkyl
$R_2$ is hydrogen or lower alkyl and
$R_3$ and $R_4$ each independently is hydrogen, halo having an atomic weight of about 19 to 35, lower alkyl or lower alkoxy and pharmaceutically acceptable acid addition salts thereof.

2. A compound according to claim 1 in the form of a pharmaceutically acceptable acid addition salt.

3. A compound according to claim 1 in which $R_3$ and $R_4$ are hydrogen.

4. A compound according to claim 1, in which $R_1$ and $R_2$ are methyl.

5. The compound according to claim 1 which is 7,13-dihydro-6,12-dimethyl-7,12-methano-6H-dibenz[c,f]azocine.

6. The compound according to claim 1, which is 7,13-dihydro-12-methyl-7,12-methano-6H-dibenz[c,f]azocine.

7. The compound according to claim 1, which is 7,13-dihydro-6-ethyl-12-methyl-7,12-methano-6H-dibenz[c,f]azocine.

8. The compound according to claim 1, which is 2-chloro-7,13-dihydro-6,12-dimethyl-7,12-methano-6H-dibenz[c,f]azocine.

9. The compound according to claim 1, which is 7,13-dihydro-2,6,12-trimethyl-7,12-methano-6H-dibenz[c,f]azocine.

10. The compound according to claim 1, which is 7,13-dihydro-6,12-dimethyl-2-methoxy-7,12-methano-6H-dibenz[c,f]azocine.

11. The compound according to claim 1, which is 9-chloro-7,13-dihydro-6,12-dimethyl-7,12-methano-6H-dibenz[c,f]azocine.

12. The compound according to claim 1, which is 7,13-dihydro-6,9,12-trimethyl-7,12-methano-6H-dibenz[c,f]azocine.

13. The compound according to claim 1, which is 7,13-dihydro-6,12-dimethyl-9-methoxy-7,12-methano-6H-dibenz[c,f]azocine.

14. A process for preparing a compound according to claim 1 which comprises cyclizing a compound of the formula

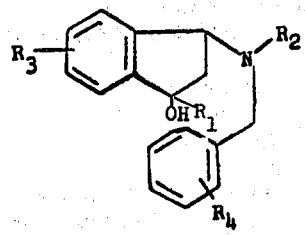

where $n$, $R_1$, $R_2$, $R_3$ and $R_4$ are as defined in claim 1 in a strong acid selected from the group consisting of polyphosphoric acid and concentrated sulfuric acid.

15. A compound according to claim 1 of the formula:

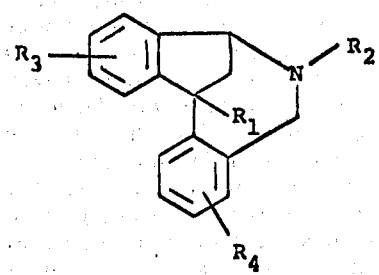

where
$R_1$ is straight chain lower alkyl
$R_2$ is hydrogen or lower alkyl and
$R_3$ and $R_4$ each independently is hydrogen, halo having an atomic weight of about 19 to 35, lower alkyl or lower alkoxy.

* * * * *